United States Patent
Kim et al.

(10) Patent No.: US 11,869,203 B2
(45) Date of Patent: Jan. 9, 2024

(54) DENTAL IMAGE REGISTRATION DEVICE AND METHOD

(71) Applicant: DIO CORPORATION, Busan (KR)

(72) Inventors: Jin Cheol Kim, Busan (KR); Jin Baek Kim, Busan (KR)

(73) Assignee: DIO CORPORATION, Busan (KR)

( * ) Notice: Subject to any disclaimer, the term of this patent is extended or adjusted under 35 U.S.C. 154(b) by 168 days.

(21) Appl. No.: 17/598,602

(22) PCT Filed: Feb. 26, 2020

(86) PCT No.: PCT/KR2020/002753
§ 371 (c)(1),
(2) Date: Sep. 27, 2021

(87) PCT Pub. No.: WO2020/197109
PCT Pub. Date: Oct. 1, 2020

(65) Prior Publication Data
US 2022/0156952 A1   May 19, 2022

(30) Foreign Application Priority Data

Mar. 28, 2019 (KR) .................. 10-2019-0036022
Mar. 28, 2019 (KR) .................. 10-2019-0036023

(51) Int. Cl.
*G06K 9/00* (2022.01)
*G06T 7/30* (2017.01)
(Continued)

(52) U.S. Cl.
CPC .............. *G06T 7/30* (2017.01); *G06T 7/13* (2017.01); *A61B 5/055* (2013.01); *A61B 6/14* (2013.01);
(Continued)

(58) Field of Classification Search
CPC ... G06T 7/30; G06T 7/13; G06T 2207/30036; G06T 2207/10028; G06T 2207/10072;
(Continued)

(56) References Cited

U.S. PATENT DOCUMENTS

| | | |
|---|---|---|
| 2002/0037489 A1 | 3/2002 | Jones et al. |
| 2010/0124367 A1* | 5/2010 | Cizek ............... G06T 7/33 382/132 |

(Continued)

FOREIGN PATENT DOCUMENTS

| | | |
|---|---|---|
| CN | 103886306 | 6/2017 |
| CN | 109146867 | 1/2019 |

(Continued)

OTHER PUBLICATIONS

Sonka, Milan Fitzpatrick, J. Michael. (2009). Handbook of Medical Imaging, vol. 2—Medical Image Processing and Analysis—8. Image Registration. SPIE. Retrieved from https://app.knovel.com/hotlink/pdf/id:kt0087DEA5/handbook-medical-imaging/image-registration (Year: 2009).*

(Continued)

*Primary Examiner* — Alex Kok S Liew
(74) *Attorney, Agent, or Firm* — CANTOR COLBURN LLP

(57) ABSTRACT

Provided is a dental image registration device comprising: an outermost boundary detection unit for detecting, from first teeth image data, a first outermost boundary region which is the outermost boundary region of dentition, and detecting, from second teeth image data, a second outermost boundary region which is the outermost boundary region of the dentition; and an image registration unit which registers the first and second teeth image data on the basis of a first inscribed circle inscribed within the first outermost boundary region and a second inscribed circle inscribed within the (Continued)

outermost boundary region, or registers the first and second teeth image data on the basis of a first central point of the first outermost boundary region and a second central point of the second outermost boundary region.

19 Claims, 13 Drawing Sheets

(51) Int. Cl.
  *G06T 7/13* (2017.01)
  *A61B 5/055* (2006.01)
  *A61B 6/14* (2006.01)
  *A61B 6/00* (2006.01)
(52) U.S. Cl.
  CPC ... *A61B 6/5247* (2013.01); *G06T 2207/30036* (2013.01)
(58) Field of Classification Search
  CPC ............. G06T 7/33; G06T 2207/10081; G06T 7/0012; G06T 2207/10116; G06T 7/11; G06T 7/73; G06T 17/00; G06T 2207/20021; G06T 2207/20156; G06T 2207/30204; G06T 7/174; G06T 7/187; G06T 7/223; G06T 2210/41; G06T 7/70; G06T 7/74; G06T 15/08; G06T 17/30; G06T 19/20; G06T 2200/04; G06T 2200/24; G06T 2207/30008; G06T 2215/16; G06T 2219/2004; G06T 7/0014; G06T 7/10; A61B 5/055; A61B 6/14; A61B 6/5247; A61B 6/032; A61B 2090/364; A61B 6/583; A61B 6/5264; A61B 5/4547; A61B 6/5258; A61B 1/247; A61B 2090/392; A61B 5/0088; A61B 5/1178; A61B 6/547; A61B 90/39; A61B 5/0073; A61C 9/0053
  See application file for complete search history.

(56) References Cited

U.S. PATENT DOCUMENTS

2013/0022251 A1* 1/2013 Chen .................... G06T 3/0031
                                                     382/131
2018/0005371 A1* 1/2018 Sabina ................... G06T 17/00

FOREIGN PATENT DOCUMENTS

| KR | 100998311   | 12/2010 |
| KR | 20120009998 | 2/2012  |
| KR | 20120042192 | 5/2012  |
| KR | 101666050   | 10/2016 |
| KR | 20170118540 | 10/2017 |
| KR | 20180047850 | 5/2018  |
| KR | 20180106451 | 10/2018 |
| WO | 2016108453  | 7/2016  |

OTHER PUBLICATIONS

"Inscribed figure", Wikipedia, Feb. 11, 2018. Retrieved from the Internet: URL: https://en.wikipedia.org/w/index.php?title=Inscribed_figure&oldid=825108444 [retrieved on Nov. 15, 2022].
"Inscribed sphere", Wikipedia, Dec. 5, 2017. Retrieved from the Internet: URL: https://en.wikipedia.org/w/index.php?title=Inscribed_sphere&oldid=813739266 [retrieved on Nov. 15, 2022].
Brown, A Survey of Image Registration Techniques, ACM Computing Surveys, vol. 24, No. 4, Dec. 1992.
Chen et al., Innovative Methodology for Multi-View Point Cloud Registration in Robotic 3D Object Scanning and Reconstruction, Appl. Sci., 2016, vol. 6, No. 5, pp. 132.
European Search Report—European Application No. 20779991.7 dated Nov. 23, 2022, citing WO 2016/108453, Chen et al., US 2002/0037489, KR 2017-0118540, Brown, "Inscribed figure" from Wikipedia, and "Inscribed sphere" from Wikipedia.
International Search Report—PCT/KR2020/002753 dated Jun. 24, 2020.

* cited by examiner

FIG. 14
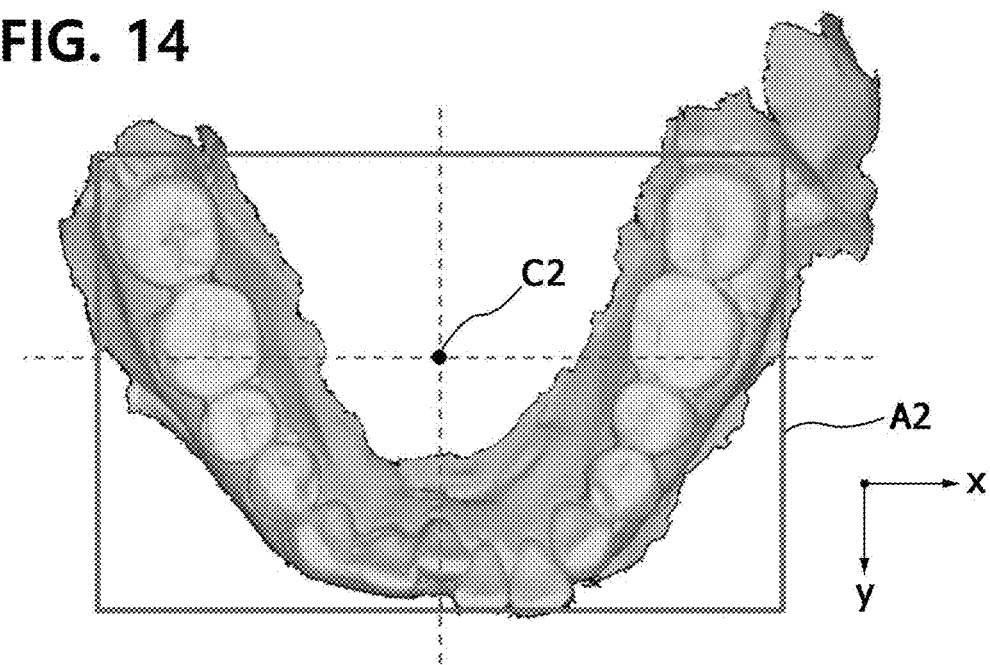
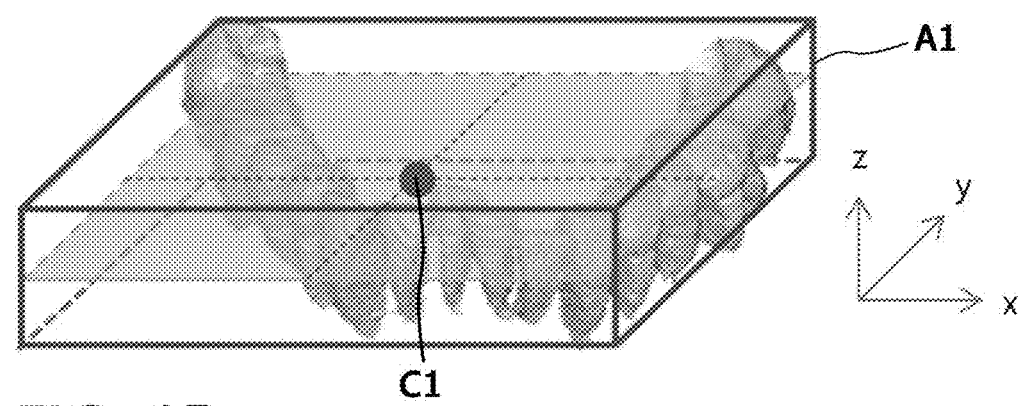
FIG. 15

DENTAL IMAGE REGISTRATION DEVICE AND METHOD

BACKGROUND

1. Field of the Invention

The present invention relates to a dental image registration device and method, and more particularly, to a dental image registration device and method capable of registering teeth images with relatively high accuracy and high speed.

2. Discussion of Related Art

In computer vision, when one scene or object is photographed at different times or viewpoints, images according to different coordinate systems are acquired. Image registration refers to the process of transforming such different images and displaying the transformed images in one coordinate system.

Through such image registration, it is possible to check a correspondence between images acquired using different measurement methods.

In dental surgical guide software, an image registration process of computed tomography (CT) image data and oral scan image data is performed generally before entering a dental implant planning stage.

The images registered through the image registration process become the basis for dental implant planning work that determines safe and optimal dental implant placement positions by identifying bone tissue and neural tube positions, and thus the accuracy of the image registration is very important for the subsequent procedure.

In an image registration method provided by the conventional medical software, users manually input a point that is a reference point for image registration, and thus image registration is performed based on the point. According to the conventional image registration method, since the user selects the reference point by roughly checking by his or her eye, a result of the image registration is very inaccurate and the user's manual operation process inevitably follows after the image registration. That is, the user modifies the result of the image registration by changing a position of the point or reselecting the point. As described above, according to the related art, there is a problem in that the user spends a long time on image registration due to the continuous repetition of registration and modification and the user may not obtain a result that is as satisfactory as the time spent.

As another conventional image registration method, there may be a method of acquiring an image including a marker for use as an intraoral registration standard and registering images acquired from a heterogeneous imaging device with respect to the marker in the image. However, the method has a problem in that it is cumbersome and causes inconvenience to patients because a process of marking for registration in the patient's mouth is a prerequisite to acquiring the images.

In the above conventional image registration methods, there is a problem in that, since the images are registered by comparing distances between all vertices included in the images, an image registration speed is reduced and system load for comparing the distances between the vertices is increased.

Therefore, there is a need for a method capable of automatically performing image registration with high speed and high accuracy without the use of a separate marker or the inconvenience of manual operation.

In addition, the conventional methods have a problem in that, since there are many unnecessary noise components such as a gum region, the accuracy of image registration is lowered.

SUMMARY OF THE INVENTION

The present invention is directed to providing a dental image registration device and method capable of improving an image registration speed and minimizing system load.

The present invention is also directed to providing a dental image registration device and method capable of improving user convenience by automatically performing image registration with high accuracy, thereby reducing a time required for dental implant planning and improving the accuracy of dental implant planning.

One aspect of the present invention provides a dental image registration device including an outermost boundary detection unit configured to detect a first outermost boundary region, which is an outermost boundary region of dentition, from first teeth image data and detect a second outermost boundary region, which is the outermost boundary region of the dentition, from second teeth image data, and an image registration unit configured to register the first and second teeth image data with respect to a first inscribed circle inscribed in the first outermost boundary region and a second inscribed circle inscribed in the second outermost boundary region or register the first and second teeth image data with respect to a first central point of the first outermost boundary region and a second central point of the second outermost boundary region.

The dental image registration device may further include an inscribed circle detection unit configured to detect the first inscribed circle inscribed in the first outermost boundary region and detect the second inscribed circle inscribed in the second outermost boundary region and an inscribed sphere detection unit configured to detect a first inscribed sphere, which is a rotation body of the first inscribed circle, and detect a second inscribed sphere, which is a rotation body of the second inscribed circle, wherein the image registration unit registers the first and second teeth image data with respect to the first and second inscribed spheres.

The dental image registration device may further include a central point detection unit configured to detect the first central point of the first outermost boundary region and detect the second central point of the second outermost boundary region, wherein the image registration unit registers the first and second teeth image data with respect to the first and second central points.

Here, the image registration unit may compare distances between first vertices included in the first inscribed sphere and second vertices included in the second inscribed sphere to register the first and second teeth image data.

The image registration unit may compare distances between first vertices included in the first outermost boundary region and second vertices included in the second outermost boundary region to register the first and second teeth image data.

The image registration unit may perform the registration of the first and second teeth image data repeatedly until the sum of all the distances between the first and second vertices becomes less than or equal to a reference value.

The image registration unit may perform the registration of the first and second teeth image data repeatedly a reference number of times.

The dental image registration device may further include a preprocessor configured to match resolutions of the first and second teeth image data and convert voxel information of the first and second teeth image data into vertex information.

The outermost boundary detection unit may detect the first and second outermost boundary regions as polygonal shapes in which each corner is in contact with a most protruding tooth.

The inscribed circle detection unit may detect two circles, which have a first radius and are each tangent to both sides that form left and right upper corners of the first and second outermost boundary regions, and one circle, which has the first radius and is tangent to a point at which a bisector line that bisects the first and second outermost boundary regions between the detected two circles abuts with a side that forms a lower end of the first and second outermost boundary regions, as the first and second inscribed circles.

The central point detection unit may detect the first central point using an average value of X-axis, Y-axis, and Z-axis coordinates of the first vertices and detects the second central point using an average value of X-axis, Y-axis, and Z-axis coordinates of the second vertices.

The outermost boundary detection unit may detect the first and second outermost boundary regions from the first and second teeth image data using vertices having a minimum position value and a maximum position value with respect to an X-axis, a Y-axis, and a Z-axis.

Another aspect of the present invention provides a dental image registration method including detecting a first outermost boundary region, which is an outermost boundary region of dentition, from first teeth image data, detecting a second outermost boundary region, which is the outermost boundary region of the dentition, from second teeth image data, and registering the first and second teeth image data with respect to a first inscribed circle inscribed in the first outermost boundary region and a second inscribed circle inscribed in the second outermost boundary region or registering the first and second teeth image data with respect to a first central point of the first outermost boundary region and a second central point of the second outermost boundary region.

Here, the registering of the first and second teeth image data may include detecting each of the first and second inscribed circles inscribed in a corresponding one of the first and second outermost boundary region, detecting each of the first and second inscribed spheres, which is a rotation body of a corresponding one of the first and second inscribed circle, and registering the first and second teeth image data with respect to the first and second inscribed sphere.

Further, the registering of the first and second teeth image data may include detecting the first and second central points of the first and second outermost boundary regions, and registering the first and second teeth image data with respect to the first and second central points.

According to the present invention, since images are registered by comparing distances between vertices included in inscribed spheres of first and second teeth image data or comparing distances between vertices included in outermost boundary regions of the first and second teeth image data, it is possible to improve an image registration speed and to minimize system load for comparing the distances between the vertices in comparison to a case in which the images are registered by comparing distances between all the vertices included in the first and second teeth image data.

Further, according to the present invention, it is possible to improve user convenience by automatically performing image registration with high accuracy, thereby reducing the time required for dental implant planning and improving the accuracy of dental implant planning.

The effects obtainable in the present invention are not limited to the above-described effects, and other effects that are not described may be clearly understood by those skilled in the art from the following description.

BRIEF DESCRIPTION OF THE DRAWINGS

FIGS. 13 and 14 are views for describing a method of detecting an outermost boundary region and a central point from two-dimensional (2D) teeth image data according to the second embodiment of the present invention.

FIGS. 15 and 16 are views for describing a method of detecting an outermost boundary region and a central point from three-dimensional (3D) teeth image data according to the second embodiment of the present invention.

DETAILED DESCRIPTION OF EXEMPLARY EMBODIMENTS

Figure 1:
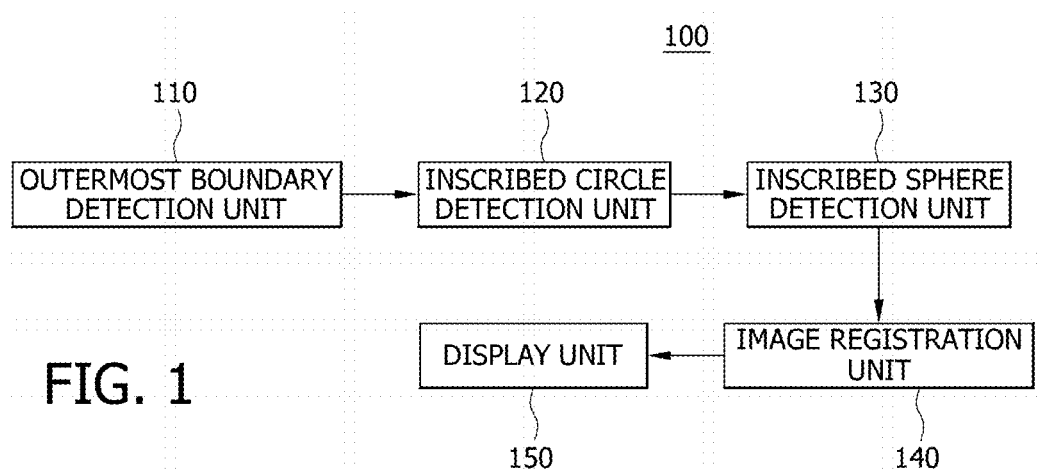
FIG. 1 is a block diagram of a dental image registration device according to a first embodiment of the present invention.

Hereinafter, embodiments of the present invention will be described in more detail with reference to the accompanying drawings. In this case, it should be noted that like reference numerals in the accompanying drawings denote like components. In addition, detailed descriptions of well-known functions and configurations that may unnecessarily obscure the gist of the present invention will not be repeated.

In the embodiments of the present invention, each component may be composed of one or more sub-components, and electrical, electronic, and mechanical functions performed by each component may be implemented with various known elements or mechanical elements, such as electronic circuits, integrated circuits, and application-specific integrated circuits (ASICs). The electrical, electronic, and mechanical functions may be implemented separately, or two or more electrical, electronic, and mechanical functions may be implemented into one function.

First Embodiment

FIG. 1 is a block diagram of a dental image registration device according to a first embodiment of the present invention.

As illustrated in FIG. 1, a dental image registration device 100 according to the first embodiment of the present invention may include an outermost boundary detection unit 110, an inscribed circle detection unit 120, an inscribed sphere detection unit 130, and an image registration unit 140.

The dental image registration device 100 according to the first embodiment of the present invention registers first teeth image data and second teeth image data.

Here, the first teeth image data and the second teeth image data are image data having different coordinate systems or resolutions due to reasons such as being acquired through different imaging devices or acquired at different time points and may each be any one of computed tomography (CT) image data, oral scan image data, and magnetic resonance image (MRI) data.

Meanwhile, although not illustrated in the drawing, the dental image registration device 100 according to the embodiment of the present invention may further include an orientation alignment unit (not illustrated) and a preprocessor (not illustrated).

Here, the orientation alignment unit (not illustrated) aligns the first teeth image data and the second teeth image data so as to face the same direction prior to image registration.

In addition, the preprocessor (not illustrated) matches resolutions of the first teeth image data and the second teeth image data by making unit distances representing an object in volume spaces of the first teeth image data and the second teeth image data be the same. In addition, the preprocessor converts voxel information of the first teeth image data and the second teeth image data into vertex information using a marching cube algorithm.

Here, the marching cube algorithm is an algorithm for extracting an isosurface from three-dimensional (3D) image data and is widely used in the corresponding image technology, and thus a detailed description thereof will be omitted.

Figure 2:
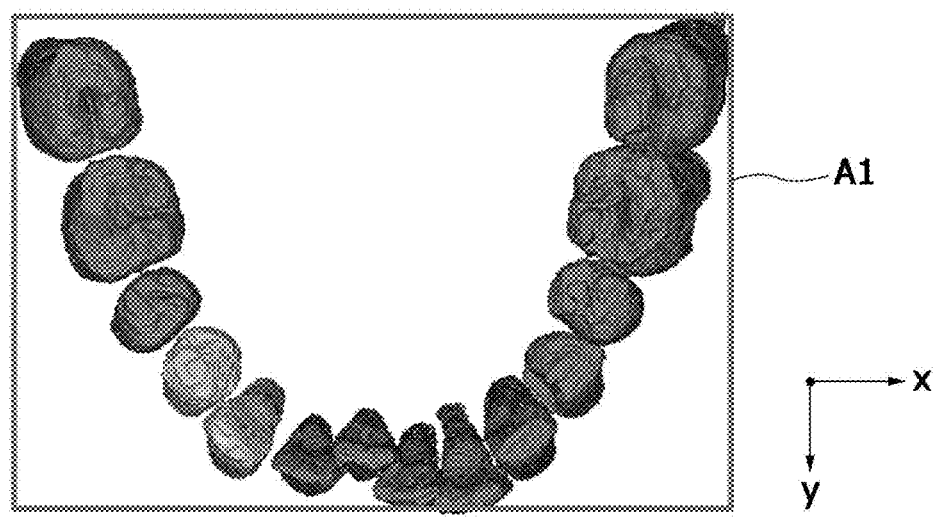
FIGS. 2 and 3 are views for describing a method of detecting an outermost boundary region from teeth image data when all teeth are provided in dentition according to the first embodiment of the present invention.
Figure 3:
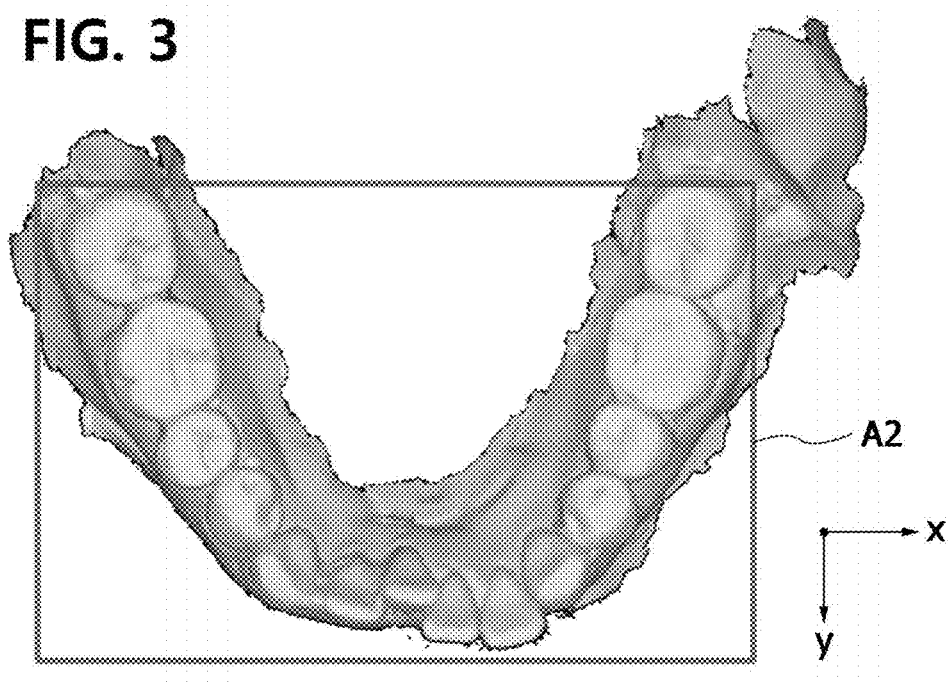
Figure 4:
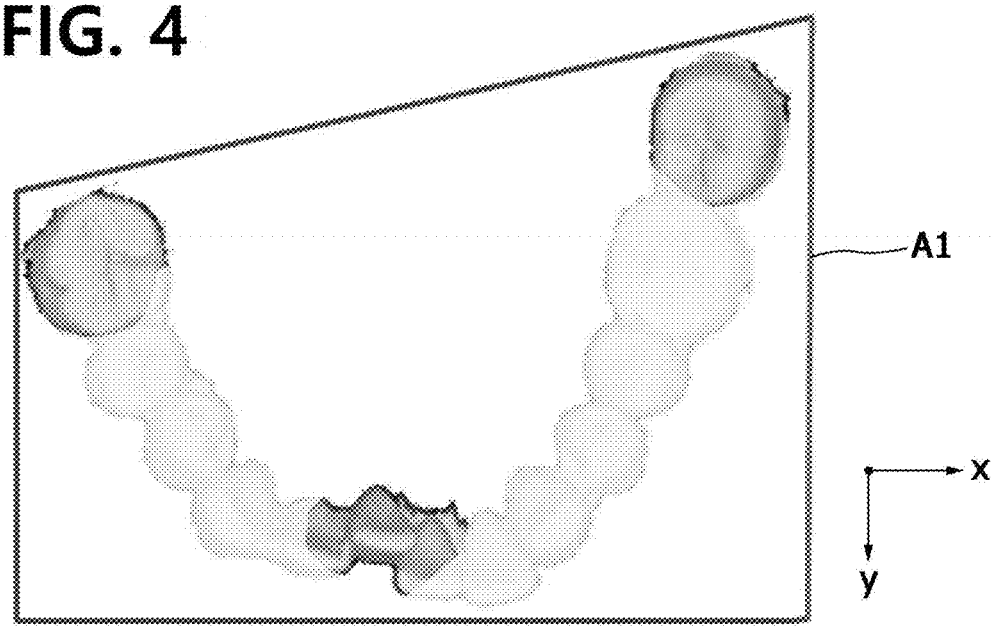
FIGS. 4 and 5 are views for describing a method of detecting an outermost boundary region from teeth image data when some teeth are absent from dentition according to the first embodiment of the present invention.
Figure 5:
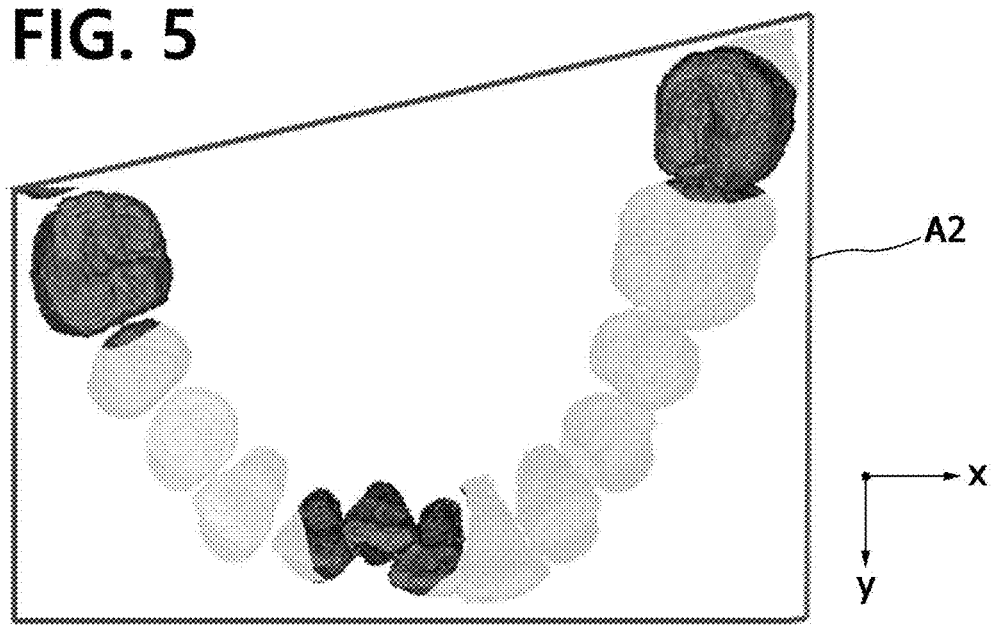

FIGS. 2 and 3 are views for describing a method of detecting an outermost boundary region from teeth image data when all teeth are provided in dentition according to the first embodiment of the present invention, and FIGS. 4 and 5 are views for describing a method of detecting an outermost boundary region from teeth image data when some teeth are absent from dentition according to the first embodiment of the present invention.

Referring to FIGS. 2 and 4, the outermost boundary detection unit 110 detects a first outermost boundary region A1, which is an outermost boundary region of dentition, from the first teeth image data. In addition, referring to FIGS. 3 and 5, the outermost boundary detection unit 110 detects a second outermost boundary region A2, which is the outermost boundary region of the dentition, from the second teeth image data.

Here, the outermost boundary regions A1 and A2 may be defined as regions in which each corner of a figure is set to be in contact with a most protruding tooth portion in a direction of the corresponding corner while taking the form of the figure that may accommodate all the teeth in the dentition. That is, the outermost boundary detection unit 110 may detect the first and second outermost boundary regions A1 and A2 as polygonal shapes in which each corner is in contact with the most protruding tooth.

For example, as illustrated in FIGS. 2 and 3, when all the teeth are provided in the dentition, the first and second outermost boundary regions A1 and A2 may be detected as rectangles and, as illustrated in FIGS. 4 and 5, when there are no teeth (e.g., molars) in the dentition, the first and second outermost boundary regions A1 and A2 may be detected as trapezoids.

The outermost boundary detection unit 110 may detect the first and second outermost boundary regions A1 and A2 in three dimensions including depth coordinates that are Z-axis coordinates within a crown length as well as in two dimensions of an X-axis and a Y-axis.

The outermost boundary detection unit 110 may perform structure and shape analysis on the first and second teeth image data and image analysis processing using an algorithm based on gray scale so that the tooth region is separated from other regions, for example, soft tissue such as gums and the like and bone tissue, and thus may detect the first and second outermost boundary regions A1 and A2 within the tooth region without including other regions.

Here, the outermost boundary detection unit 110 may detect the first and second outermost boundary regions A1 and A2 from the first and second teeth image data using vertices having a minimum position value and a maximum position value with respect to the X-axis, the Y-axis, and the Z-axis.

Specifically, vertices having a minimum position value with respect to the Y-axis are detected on lower sides of the first and second outermost boundary regions A1 and A2, and horizontal extension lines are generated to include the vertices. In addition, vertices each having a minimum position value and a maximum position value with respect to the X-axis are detected on left and right sides of the first and second outermost boundary regions A1 and A2, and vertical extension lines are generated to include the vertices. In addition, vertices each having a maximum position value in left and right regions with respect to a bisector line L bisected based on the X-axis are detected on upper sides of the first and second outermost boundary regions A1 and A2, and extension lines are generated to include the vertices. In addition, the first and second outermost boundary regions A1 and A2 having points crossing the generated extension lines as vertices are generated.

Figure 6:
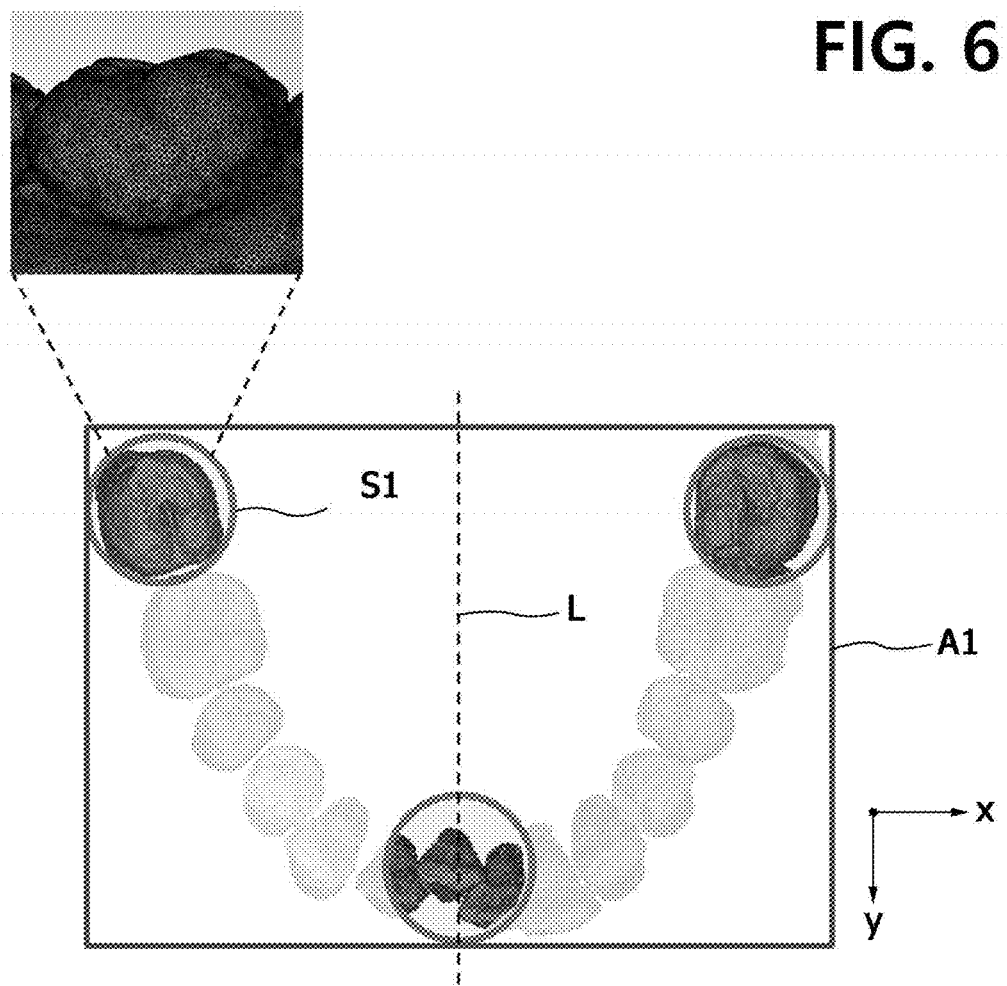
FIGS. 6 and 7 are views for describing a method of detecting an inscribed circle from an outermost boundary region when all teeth are provided in dentition according to the first embodiment of the present invention.
Figure 7:
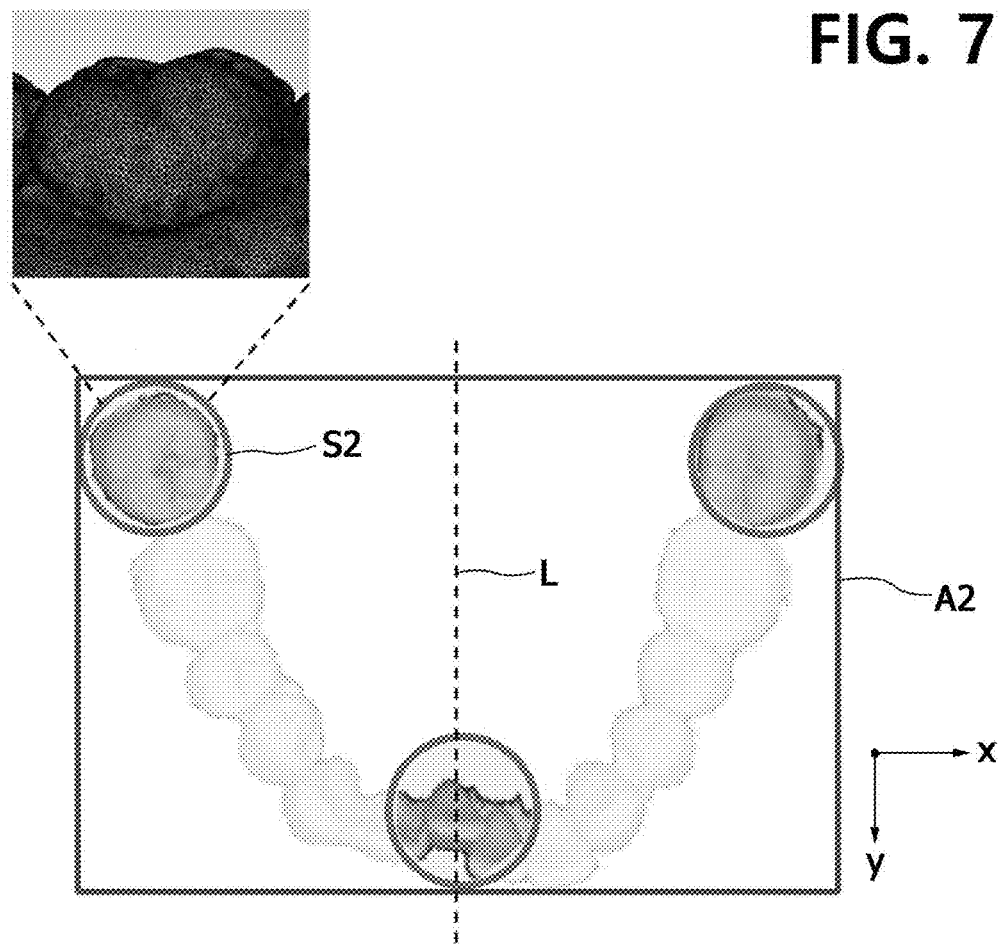
Figure 8:
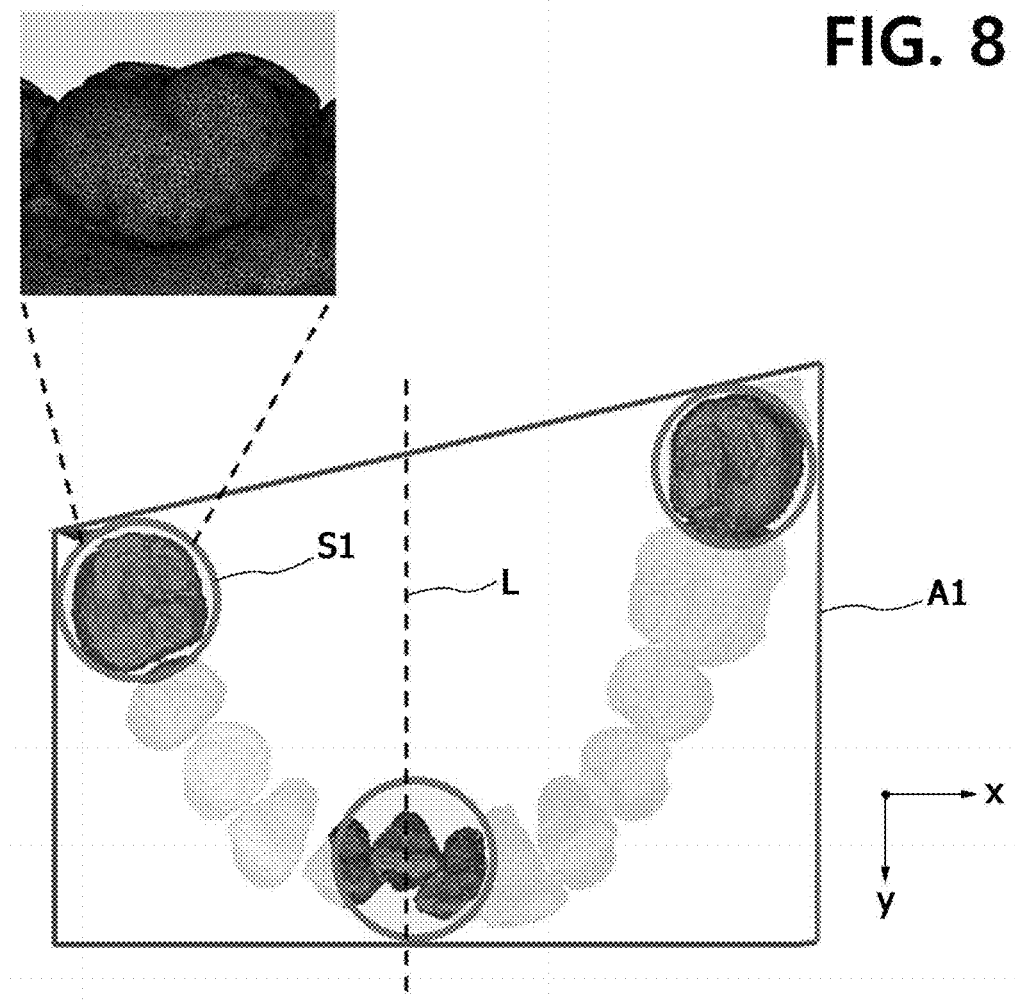
FIGS. 8 and 9 are views for describing a method of detecting an inscribed circle from an outermost boundary region when some teeth are absent from dentition according to the first embodiment of the present invention.
Figure 9:
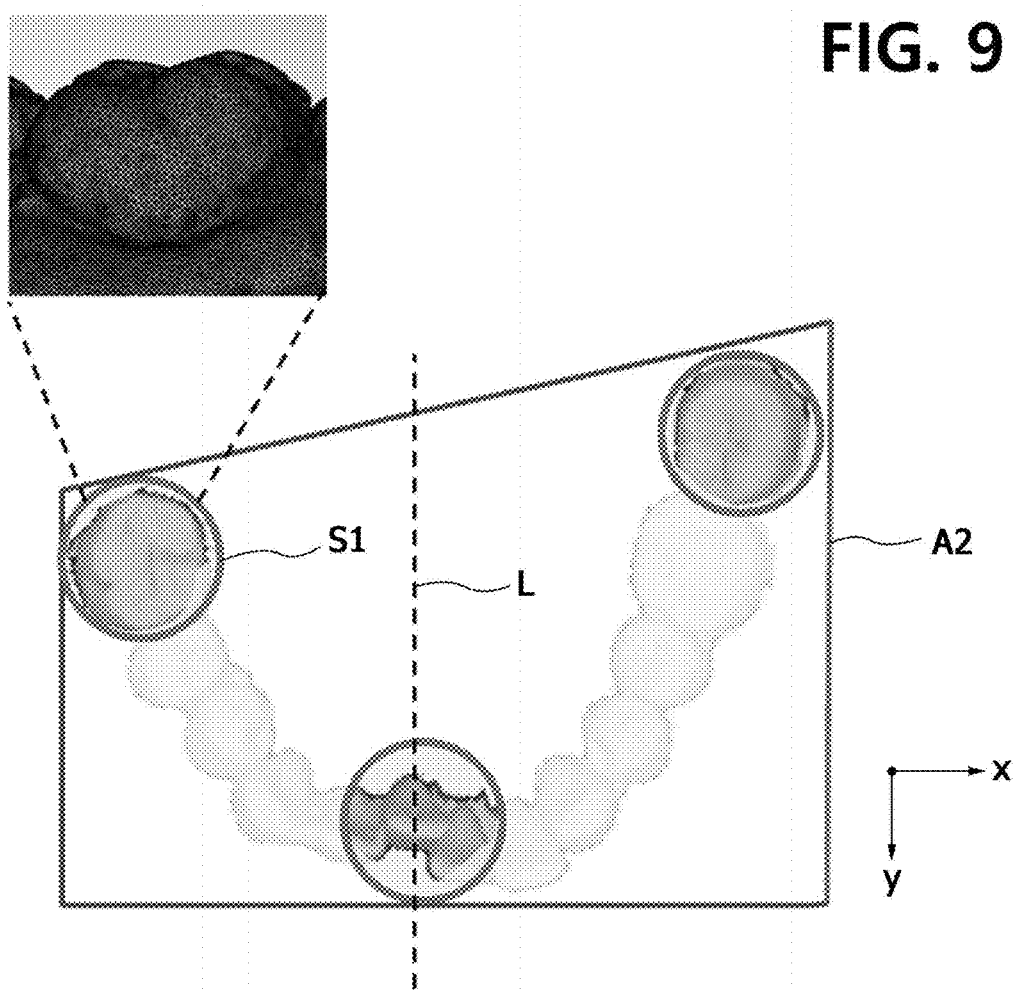

FIGS. 6 and 7 are views for describing a method of detecting an inscribed circle from an outermost boundary region when all teeth are provided in dentition according to the first embodiment of the present invention, and FIGS. 8 and 9 are views for describing a method of detecting an inscribed circle from an outermost boundary region when some teeth are absent from dentition according to the first embodiment of the present invention.

Referring to FIGS. 6 and 8, the inscribed circle detection unit 120 detects a first inscribed circle S1 inscribed in the first outermost boundary region A1. In addition, referring to FIGS. 7 and 9, the inscribed circle detection unit 120 detects a second inscribed circle S2 inscribed in the second outermost boundary region A2.

The inscribed circle detection unit 120 may detect three first inscribed circles S1 in the first outermost boundary region A1. Specifically, the inscribed circle detection unit 120 may detect two circles, which have a first radius and are each tangent to both sides that form left and right upper corners of the first outermost boundary region A1, and one circle, which has the first radius and is tangent to a point at which a bisector line L that bisects the first outermost boundary region A1 between the detected two circles abuts with a side that forms a lower end of the first outermost boundary region A1, as the first inscribed circles S1.

Similarly, the inscribed circle detection unit 120 may detect three second inscribed circles S2 in the second outermost boundary region A2. Specifically, the inscribed circle detection unit 120 may detect two circles, which have the first radius and are each tangent to both sides that form left and right upper corners of the second outermost boundary region A2, and one circle, which has the first radius and is tangent to a point at which a bisector line L that bisects the second outermost boundary region A2 between the detected two circles abuts with a side that forms a lower end of the second outermost boundary region A2, as the second inscribed circles S2.

The inscribed sphere detection unit 130 detects a first inscribed sphere which is a rotation body of the first inscribed circle S1.

Here, X-axis and Y-axis coordinates of the center of the first inscribed sphere coincide with X-axis and Y-axis coordinates of the center of the first inscribed circle S1, and X-axis and Y-axis coordinates of the center of a second inscribed sphere coincide with X-axis and Y-axis coordinates of the center of the second inscribed circle S2.

In addition, the inscribed sphere detection unit 130 may calculate an average value of Z-axis coordinates that are depth information of first vertices included in the first inscribed circle S1 as Z-axis coordinates of the center of the first inscribed sphere and may detect the first inscribed sphere having the first radius with respect to the center of the first inscribed sphere.

Similarly, the inscribed sphere detection unit 130 detects a second inscribed sphere which is a rotation body of the second inscribed circle S2.

Here, X-axis and Y-axis coordinates of the center of the second inscribed sphere coincide with the X-axis and Y-axis coordinates of the center of the second inscribed circle S2, and the X-axis and Y-axis coordinates of the center of the second inscribed sphere coincide with the X-axis and Y-axis coordinates of the center of the second inscribed circle S2.

In addition, the inscribed sphere detection unit 130 may calculate an average value of Z-axis coordinates that are depth information of second vertices included in the second inscribed circle S2 as Z-axis coordinates of the center of the second inscribed sphere and may detect the second inscribed sphere having the first radius with respect to the center of the second inscribed sphere.

Meanwhile, as described above, the detected first and second inscribed spheres may include teeth.

Figure 10:
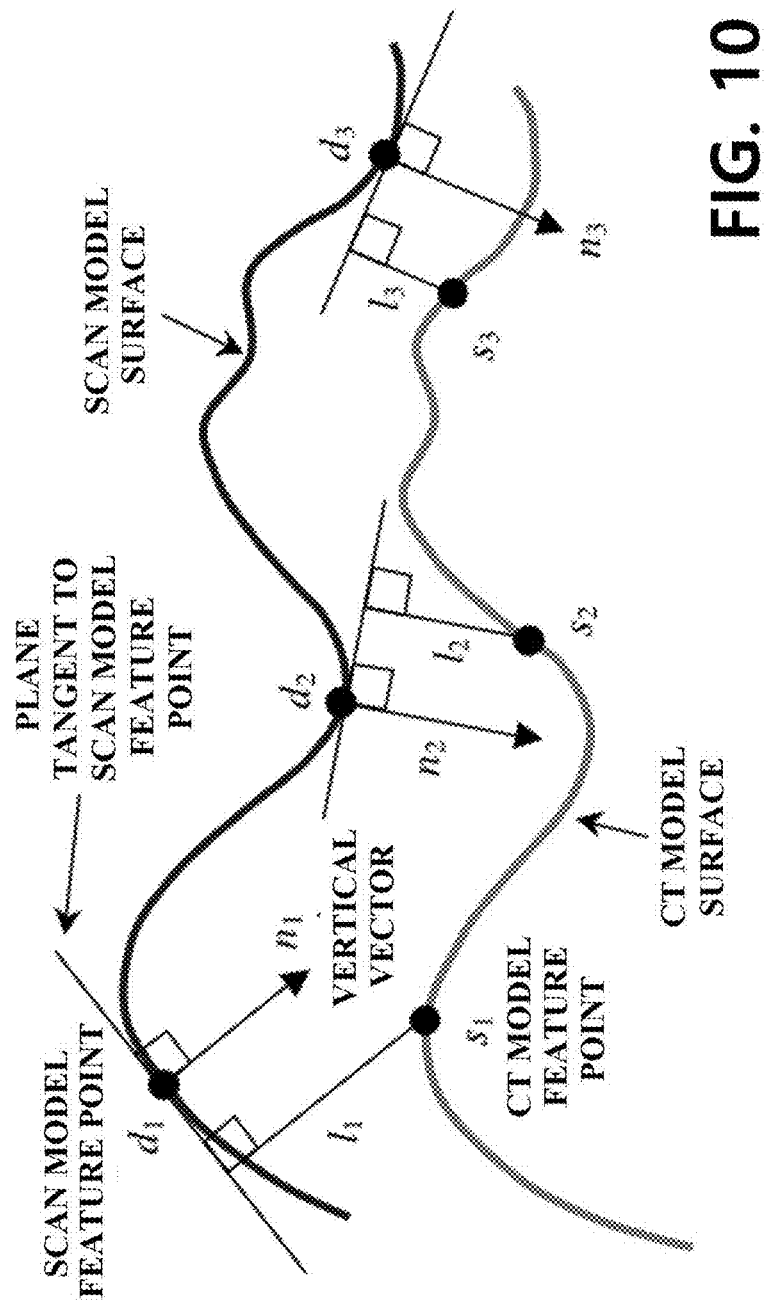
FIG. 10 is a diagram for describing a method for an image registration unit to register first and second teeth image data according to the first embodiment of the present invention.

FIG. 10 is a diagram for describing a method for an image registration unit to register first and second teeth image data according to the first embodiment of the present invention.

The image registration unit 140 registers the first and second teeth image data with respect to the first and second inscribed sphere.

Specifically, referring to FIG. 10, the image registration unit 140 overlaps the first and second teeth image data with respect to the first and second inscribed spheres and then compares distances between the first vertices included in the first inscribed sphere and the second vertices included in the second inscribed sphere to register the first teeth image data and the second teeth image data.

The image registration unit 140 may perform the registration of the first teeth image data and the second teeth image data repeatedly until the sum of all the distances between the first vertices and the second vertices becomes less than or equal to a reference value.

Here, the reference value may be preset by a user and may vary according to a target image registration accuracy. That is, as the target image registration accuracy increases, the reference value decreases.

Specifically, referring to FIG. 10, when distances between first vertices s1, s2, and s3 and second vertices d1, d2, and d3 become sufficiently small by repeatedly performing the registration process, the registration process may be repeatedly performed such that distances 11, 12, and 13 of extension lines extending from a plane that is in contact with the second vertices d1, d2, and d3 to the first vertices s1, s2, and s3 and distances between the extension lines and a vertical vector of the second vertices d1, d2, and d3 are reduced.

Alternatively, the image registration unit 140 may perform the registration of the first teeth image data and the second teeth image data repeatedly a reference number of times.

Here, the reference number of times may be preset by the user and may vary according to the target image registration accuracy. That is, since the image registration accuracy is improved as the number of times of image registration is increased, the reference number of times increases as the target image registration accuracy increases.

As described above, since the dental image registration device 100 according to the first embodiment of the present invention compares only the distances between the vertices included in the inscribed spheres of the first and second teeth image data to register the images, it is possible to improve an image registration speed and to minimize system load for comparing the distances between the vertices in comparison to the case in which the images are registered by comparing the distances between all the vertices included in the first teeth image data and the second teeth image data.

Further, in the dental image registration device 100 according to the embodiment of the present invention, it is possible to improve user convenience by automatically performing the image registration with high accuracy, thereby reducing the time required for dental implant planning and improving the accuracy of dental implant planning.

The dental image registration device 100 according to the first embodiment of the present invention may further include a display unit 150 that displays a registration result of the first teeth image data and the second teeth image data.

The display unit 150 may display the registration result of the first and second teeth image data and allow the user to check the registration result.

Specifically, the display unit 150 may provide a mark that may quantitatively grasp the accuracy of the image registration result, such as displaying a mis-registered part or a relatively inaccurate part in the registered image with different colors or the like, when displaying the registration result so that the user may objectively grasp a degree of accuracy of the registration.

The display unit 150 includes a liquid crystal display (LCD), a light-emitting diode (LED) display, an organic LED (OLED) display, a micro electro mechanical systems (MEMS) display, and an electronic paper display. Here, the display unit 150 may be implemented as a touch screen in combination with an input unit (not illustrated).

Figure 11:
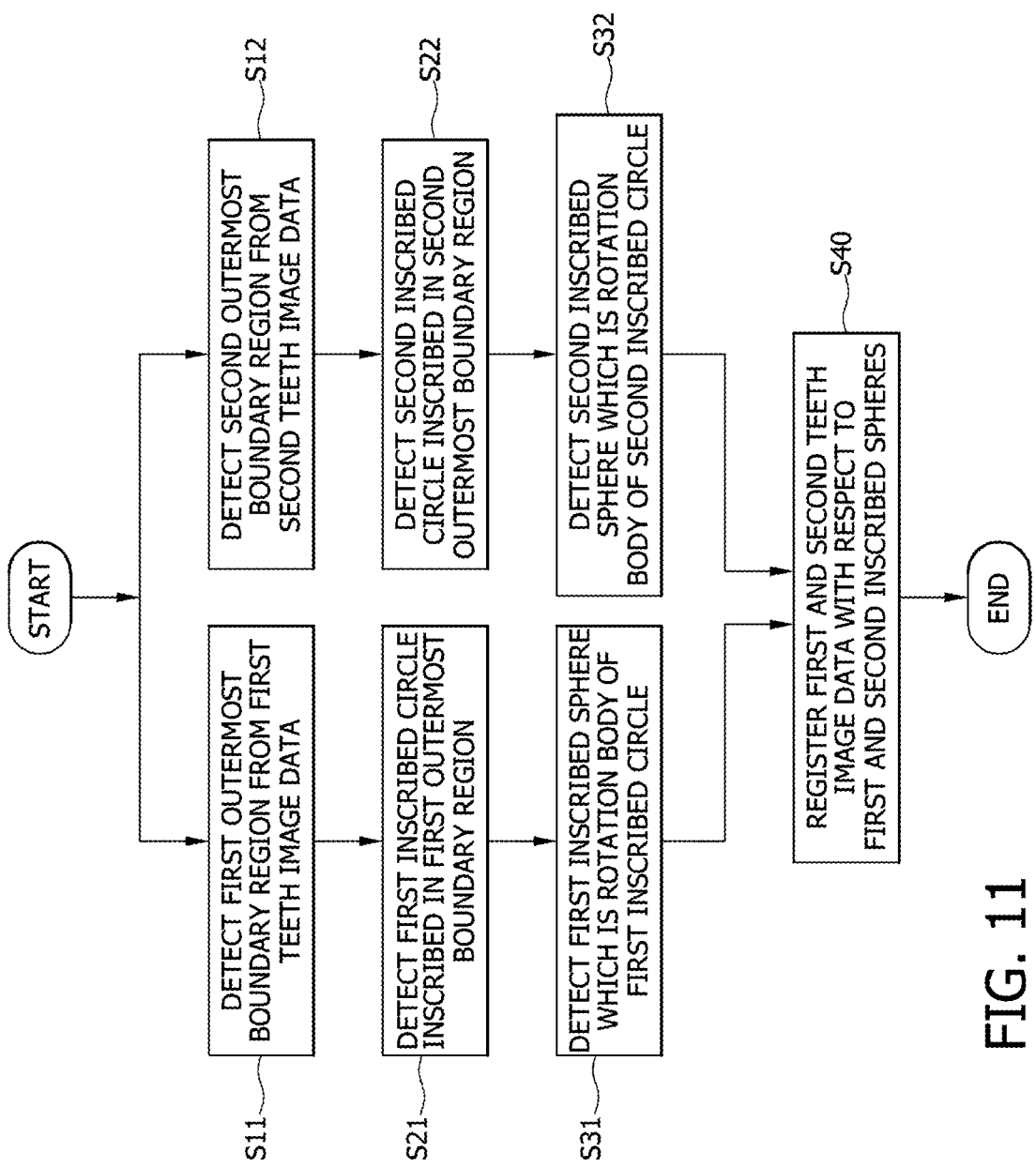
FIG. 11 is a flowchart of a dental image registration method according to the first embodiment of the present invention.

FIG. 11 is a flowchart of a dental image registration method according to the first embodiment of the present invention.

Hereinafter, the dental image registration method according to the first embodiment of the present invention will be described with reference to FIGS. 1 to 11, and the same contents as the dental image registration device according to the first embodiment of the present invention described above will be omitted.

In the dental image registration method according to the first embodiment of the present invention, first, a first outermost boundary region A1 which is an outermost boundary region of dentition is detected from first teeth image data (S11).

Next, a first inscribed circle S1 inscribed in the first outermost boundary region A1 is detected (S21) and a first inscribed sphere which is a rotation body of the first inscribed circle S1 is detected (S31).

Similarly, a second outermost boundary region A2 which is the outermost boundary region of the dentition is detected from second teeth image data (S12).

Next, a second inscribed circle S2 inscribed in the second outermost boundary region A2 is detected (S22) and a second inscribed sphere, which is a rotation body of the second inscribed circle S2, is detected (S32).

Next, the first and second teeth image data are registered with respect to the first and second inscribed spheres (S40).

Here, the operation S40 of registering the first and second teeth image data is an operation of overlapping the first and second teeth image data with respect to the first and second inscribed spheres and then comparing distances between first vertices included in the first inscribed sphere and second vertices included in the second inscribed sphere to register the first and second teeth image data.

Further, the operation S40 of registering the first and second teeth image data is an operation of performing the registration of the first and second teeth image data repeatedly until the sum of all the distances between the first and second vertices becomes less than or equal to a reference value.

Further, the operation S40 of registering the first and second teeth image data is an operation of performing the registration of the first and second teeth image data repeatedly a reference number of times.

As described above, in the dental image registration method according to the first embodiment of the present invention, since only the distances between the vertices included in the inscribed sphere of the first and second teeth image data are compared and the images are registered, it is possible to improve an image registration speed and to minimize system load for comparing the distances between the vertices in comparison to the case in which the images are registered by comparing the distances between all the vertices included in the first teeth image data and the second teeth image data.

Further, in the dental image registration method according to the first embodiment of the present invention, it is possible to improve user convenience by automatically performing the image registration with high accuracy, thereby reducing the time required for dental implant planning and improving the accuracy of dental implant planning.

Meanwhile, the dental image registration method according to the first embodiment of the present invention may be written as a program that may be executed on a computer and may be implemented in various recording media such as magnetic storage media, optical reading media, and digital storage media.

In the above-described first embodiment, an example is described in which image registration of CT image data and oral scan image data is performed. However, for various combinations between pieces of two-dimensional (2D) image data, between 2D and 3D image data, and between pieces of 3D image data, such as between pieces of CT image data, between pieces of oral scan image data, between MRI image data and CT image data, etc., the image registration may be performed by detecting the outermost boundary region of the dentition from the image data and detecting the inscribed sphere from the outermost boundary region in the same manner as above. In this case, it is as described above that, when the outermost boundary region of the dentition is detected from the 3D image data, a final outermost boundary region of the dentition may be detected by calculating depth coordinates that are Z-axis coordinates within a crown length in consideration of the fact that a periphery of the dentition varies depending on the crown length, as well as calculating X-axis and Y-axis coordinates. Further, the above-described first embodiment is also applicable to a multidimensional image including four-dimensional (4D) image data in addition to the above-described 3D image data.

Second Embodiment

Figure 12:
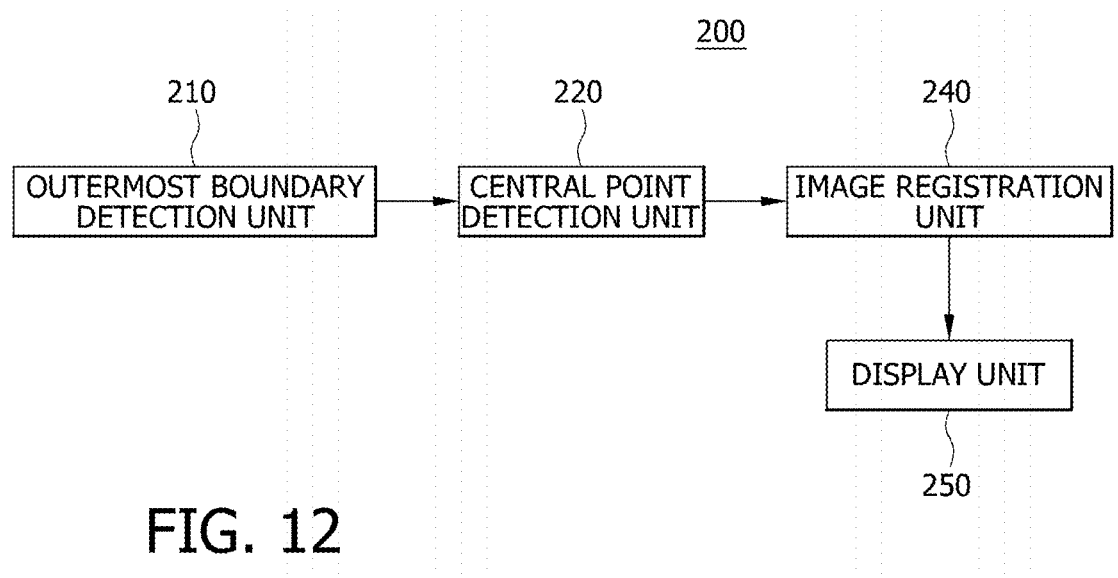
FIG. 12 is a block diagram of a dental image registration device according to a second embodiment of the present invention.

FIG. 12 is a block diagram of a dental image registration device according to a second embodiment of the present invention.

As illustrated in FIG. 12, a dental image registration device 200 according to the second embodiment of the present invention may include an outermost boundary detection unit 210, a central point detection unit 220, and an image registration unit 240.

The dental image registration device 200 according to the second embodiment of the present invention registers first teeth image data and second teeth image data.

Here, the first teeth image data and the second teeth image data are pieces of image data that have different coordinate systems or resolutions due to reasons such as being acquired through different imaging devices or being acquired at different time points and may each be any one of CT image data, oral scan image data, and MRI data.

Meanwhile, although not illustrated in the drawing, the dental image registration device 200 according to the second embodiment of the present invention may further include an orientation alignment unit (not illustrated) and a preprocessor (not illustrated).

Here, the orientation alignment unit (not illustrated) aligns the first teeth image data and the second teeth image data so as to face the same direction prior to image registration.

In addition, the preprocessor (not illustrated) matches resolutions of the first teeth image data and the second teeth image data by making unit distances representing an object in volume spaces of the first teeth image data and the second teeth image data be the same. In addition, the preprocessor converts voxel information of the first teeth image data and the second teeth image data into vertex information using a marching cube algorithm.

Here, the marching cube algorithm is an algorithm for extracting an isosurface from 3D image data and is widely used in the corresponding image technology, and thus a detailed description thereof will be omitted.

Figure 13:
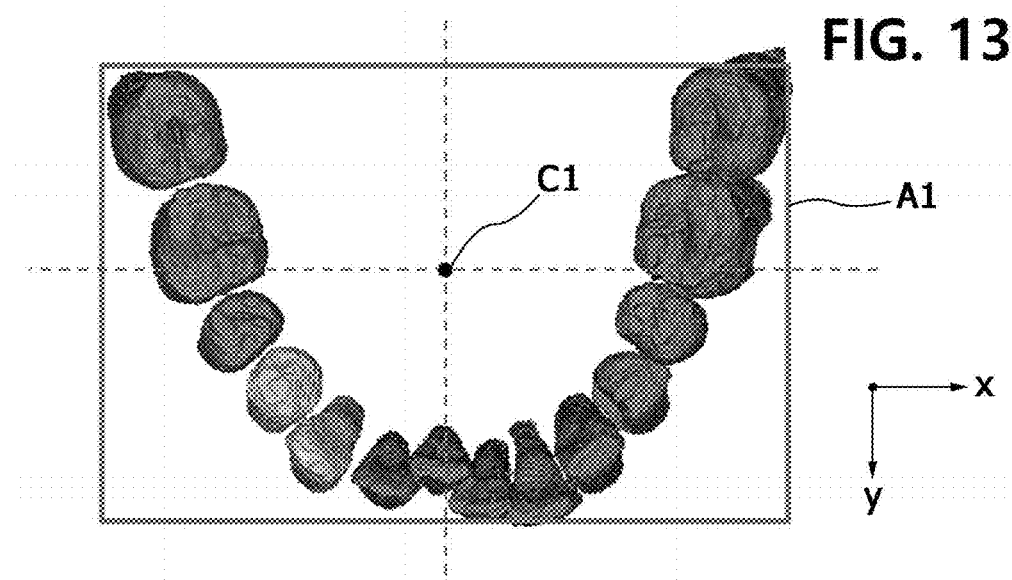
Figure 16:
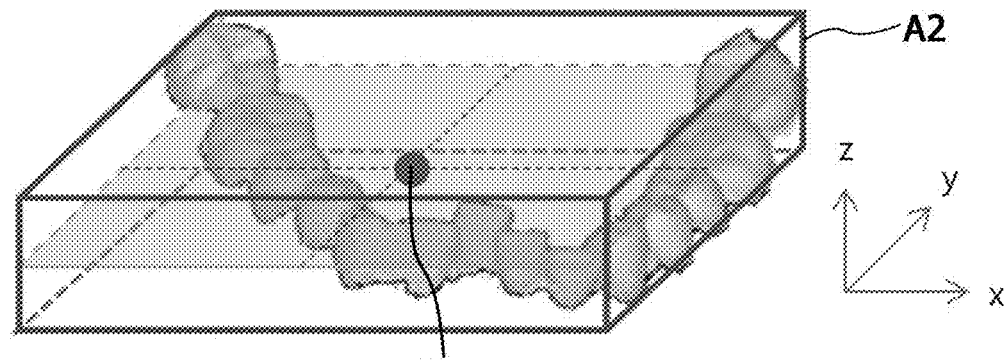

FIGS. 13 and 14 are views for describing a method of detecting an outermost boundary region and a central point from 2D teeth image data according to the second embodiment of the present invention, and FIGS. 15 and 16 are views for describing a method of detecting an outermost boundary region and a central point from 3D teeth image data according to the second embodiment of the present invention.

Referring to FIG. 13, the outermost boundary detection unit 210 detects a first outermost boundary region A1, which is an outermost boundary region of dentition, from the first teeth image data. In addition, referring to FIG. 14, the outermost boundary detection unit 210 detects a second outermost boundary region A2, which is the outermost boundary region of the dentition, from the second teeth image data.

Here, the outermost boundary regions A1 and A2 may be defined as regions in which each corner of a figure is set to be in contact with a most protruding tooth portion in a direction of the corresponding corner while taking the form of the figure that may accommodate all teeth in the dentition. That is, the outermost boundary detection unit 210 may detect the first and second outermost boundary regions A1 and A2 as polygonal shapes in which each corner is in contact with the most protruding tooth.

For example, as illustrated in FIGS. 13 and 14, when all teeth are provided in the dentition, the first and second outermost boundary regions A1 and A2 may be detected as rectangles.

Meanwhile, unlike the drawing, when there are no teeth (e.g., molars) in the dentition, the first and second outermost boundary regions A1 and A2 may be detected as trapezoids.

Referring to FIGS. 15 and 16, the outermost boundary detection unit 210 may detect the first and second outermost boundary regions A1 and A2 in three dimensions including depth coordinates that are Z-axis coordinates within a crown length as well as in two dimensions of an X-axis and a Y-axis.

The outermost boundary detection unit 210 may perform structure and shape analysis on the first and second teeth image data and image analysis processing using an algorithm based on gray scale so that the tooth region is separated from other regions, for example, soft tissue such as gums and the like and bone tissue and thus may detect the first and second outermost boundary regions A1 and A2 within the tooth region without including other regions.

Here, the outermost boundary detection unit 210 may detect the first and second outermost boundary regions A1 and A2 from the first and second teeth image data using vertices having a minimum position value and a maximum position value with respect to the X-axis, the Y-axis, and the Z-axis.

Specifically, vertices having a minimum position value with respect to the Y-axis are detected on lower sides of the first and second outermost boundary regions A1 and A2, and horizontal extension lines are generated to include the vertices. In addition, vertices each having a minimum position value and a maximum position value with respect to the X-axis are detected on left and right sides of the first and second outermost boundary regions A1 and A2, and vertical extension lines are generated to include the vertices. In addition, vertices each having a maximum position value in left and right regions with respect to a bisector line bisected based on the X-axis are detected on upper sides of the first and second outermost boundary regions A1 and A2, and extension lines are generated to include the vertices. In addition, the first and second outermost boundary regions A1 and A2 having points crossing the generated extension lines as vertices are generated.

Referring to FIG. 13, the central point detection unit 220 detects a first central point C1 of a first 2D outermost boundary region A1. In addition, referring to FIG. 14, the central point detection unit 220 detects a second central point C2 of a second 2D outermost boundary region A2.

Specifically, the central point detection unit 220 detects the first central point C1 using an average value of X-axis and Y-axis coordinates of first vertices included in the first outermost boundary region A1. In addition, the central point detection unit 220 detects the second central point C2 using an average value of X-axis and Y-axis coordinates of second vertices included in the second outermost boundary region A2.

Further, referring to FIG. 15, the central point detection unit 220 detects a first central point C1 of a first 3D outermost boundary region A1. In addition, referring to FIG. 16, the 3D the central point detection unit 220 detects a second central point C2 of a second 3D outermost boundary region A2.

Specifically, the central point detection unit 220 detects the first central point C1 using an average value of X-axis, Y-axis, and Z-axis coordinates of first vertices included in the first outermost boundary region A1. In addition, the central point detection unit 220 detects the second central point C2 using an average value of X-axis, Y-axis, and Z-axis coordinates of second vertices included in the second outermost boundary region A2.

Figure 17:
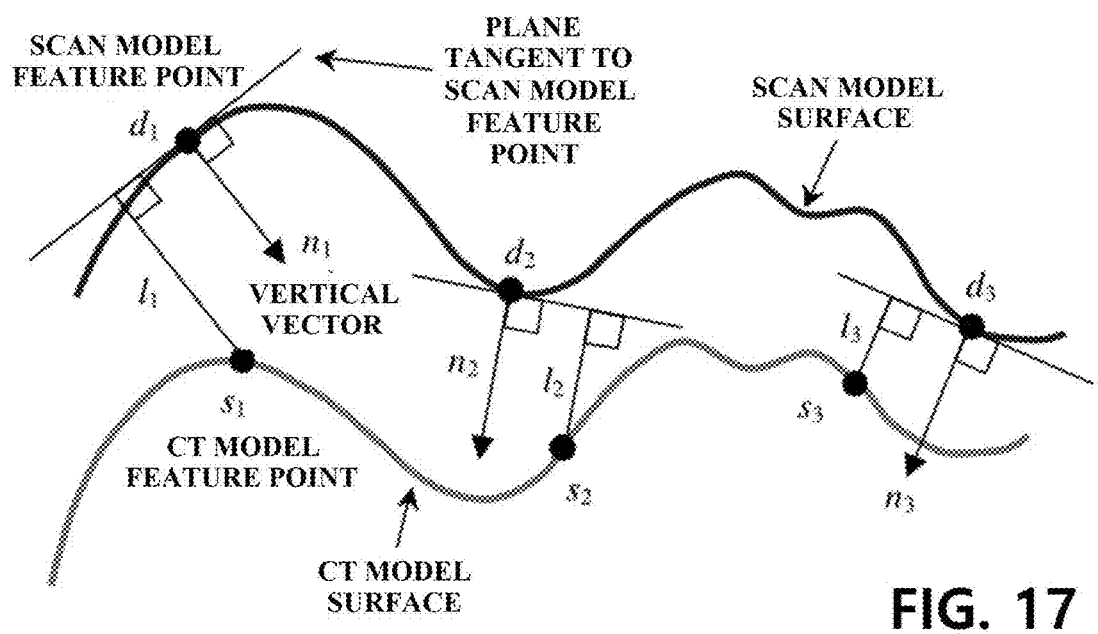
FIG. 17 is a diagram for describing a method for an image registration unit to register first and second teeth image data according to the second embodiment of the present invention.

FIG. 17 is a diagram for describing a method for an image registration unit to register first and second teeth image data according to the second embodiment of the present invention.

The image registration unit 240 registers the first and second teeth image data with respect to the first and second central points C1 and C2.

Specifically, referring to FIG. 17, the image registration unit 240 overlaps the first and second teeth image data with respect to the first and second central points C1 and C2 and then compares distances between the first vertices included in the first outermost boundary region A1 and the second vertices included in the second outermost boundary region A2 to register the first teeth image data and the second teeth image data.

The image registration unit 240 may perform the image registration of the first teeth image data and the second teeth image data repeatedly until the sum of all the distances between the first vertices and the second vertices becomes less than or equal to a reference value.

Here, the reference value may be preset by the user and may vary according to a target image registration accuracy. That is, as the target image registration accuracy increases, the reference value decreases.

Specifically, referring to FIG. 17, when distances between first vertices s1, s2, and s3 and second vertices d1, d2, and d3 become sufficiently small by repeatedly performing the registration process, the registration process may be repeatedly performed such that distances 11, 12, and 13 of extension lines extending from a plane that is in contact with the second vertices d1, d2, and d3 to the first vertices s1, s2, and s3 and distances between the extension lines and a vertical vector of the second vertices d1, d2, and d3 are reduced.

Alternatively, the image registration unit 240 may perform the image registration of the first teeth image data and the second teeth image data repeatedly a reference number of times.

Here, the reference number of times may be preset by the user and may vary according to the target image registration accuracy. That is, since the image registration accuracy is improved as the number of times of image registration is increased, the reference number of times increases as the target image registration accuracy increases.

As described above, since the dental image registration device 200 according to the second embodiment of the present invention compares only the distances between the vertices included in the first and second outermost boundary regions A1 and A2 of the first and second teeth image data to register the images, it is possible to improve an image registration speed and to minimize system load for comparing the distances between the vertices in comparison to the case in which the images are registered by comparing the distances between all the vertices included in the first teeth image data and the second teeth image data.

Further, in the dental image registration device 200 according to the second embodiment of the present invention, it is possible to improve user convenience by automatically performing the image registration with high accuracy, thereby reducing the time required for dental implant planning and improving the accuracy of dental implant planning.

The dental image registration device 200 according to the second embodiment of the present invention may further include a display unit 250 that displays a registration result of the first teeth image data and the second teeth image data.

The display unit 250 may display the registration result of the first and second teeth image data and allow the user to check the registration result.

Specifically, the display unit 250 may provide a mark that may quantitatively grasp the accuracy of the image registration result, such as displaying a mis-registered part or a relatively inaccurate part in the registered image with different colors or the like, when displaying the registration result so that the user may objectively grasp a degree of accuracy of the registration.

The display unit 250 includes an LCD, an LED display, an OLED display, an MEMS display, and an electronic paper display. Here, the display unit 250 may be implemented as a touch screen in combination with an input unit (not illustrated).

Figure 18:
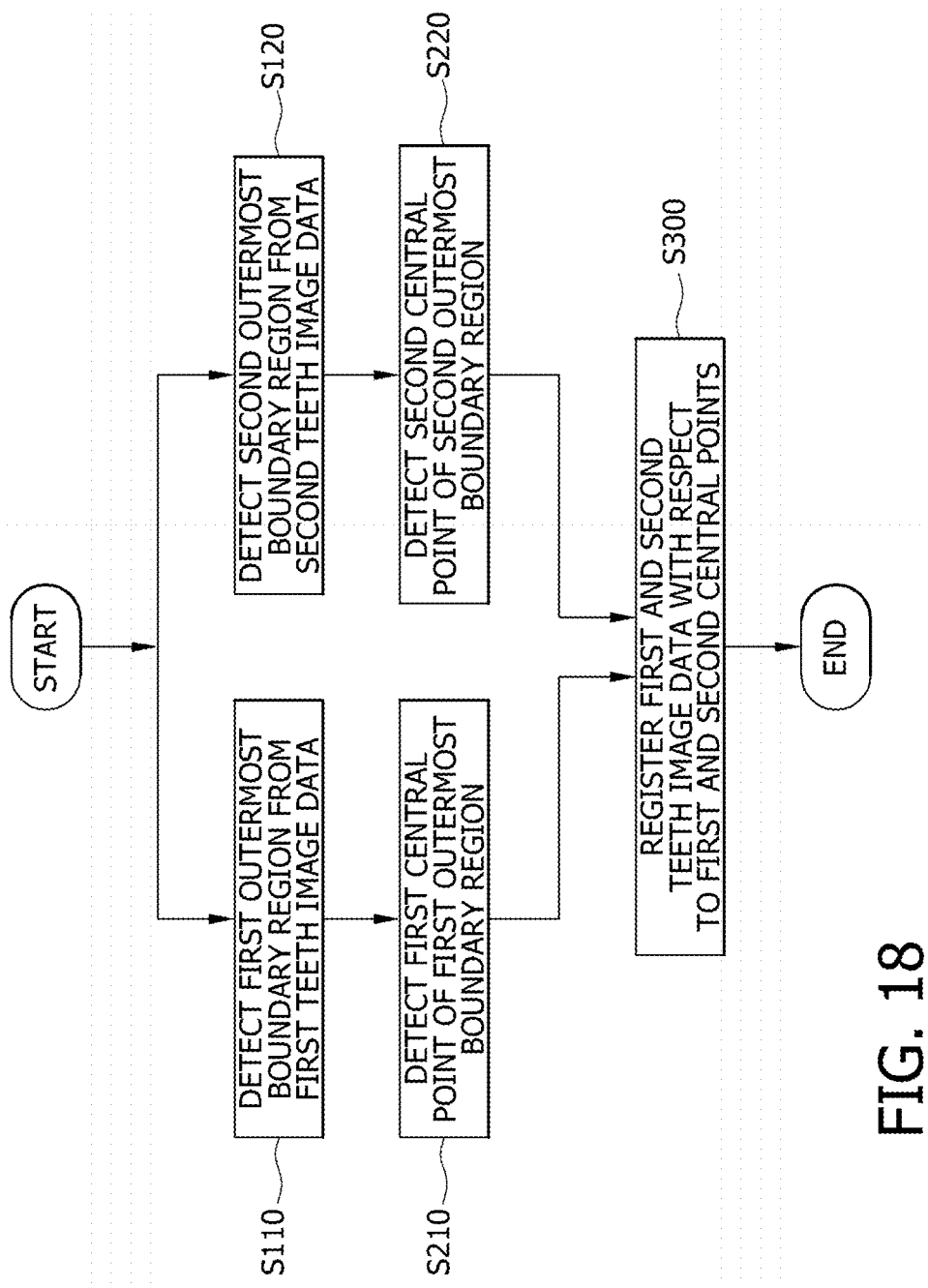
FIG. 18 is a flowchart of a dental image registration method according to the second embodiment of the present invention.

FIG. 18 is a flowchart of a dental image registration method according to the second embodiment of the present invention.

Hereinafter, the dental image registration method according to the second embodiment of the present invention will be described with reference to FIGS. 12 to 18 and the same contents as the dental image registration device according to the second embodiment of the present invention described above will be omitted.

In the dental image registration method according to the second embodiment of the present invention, first, a first outermost boundary region A1 which is an outermost boundary region of dentition is detected from first teeth image data (S110).

Next, a first central point C1 of the first outermost boundary region A1 is detected (S210).

Similarly, a second outermost boundary region A2 which is the outermost boundary region of the dentition is detected from the second teeth image data (S120).

Next, a central point C2 of the second outermost boundary region A2 is detected (S220).

Next, the first and second teeth image data are registered with respect to the first and second central points C1 and C2 (S300).

Here, the operation S300 of registering the first and second teeth image data is an operation of overlapping the first and second teeth image data with respect to the first and second central points C1 and C2 and then comparing distances between first vertices included in the first outermost boundary region A1 and second vertices included in the second outermost boundary region A2 to register the first and second teeth image data.

Further, the operation S300 of registering the first and second teeth image data is an operation of performing the registration of the first and second teeth image data repeatedly until the sum of all the distances between the first and second vertices becomes less than or equal to a reference value.

Further, the operation S300 of registering the first and second teeth image data is an operation of performing the registration of the first and second teeth image data repeatedly a reference number of times.

As described above, in the dental image registration method according to the second embodiment of the present invention, since only the distances between the vertices included in the first and second outermost boundary regions of the first and second teeth image data are compared and the images are registered, it is possible to improve an image registration speed and to minimize system load for comparing the distances between the vertices in comparison to the case in which the images are registered by comparing the distances between all the vertices included in the first teeth image data and the second teeth image data.

Further, in the dental image registration method according to the second embodiment of the present invention, it is possible to improve user convenience by automatically performing the image registration with high accuracy, thereby reducing the time required for dental implant planning and improving the accuracy of dental implant planning.

Meanwhile, the dental image registration method according to the second embodiment of the present invention may be written as a program that may be executed on a computer and may be implemented in various recording media such as magnetic storage media, optical reading media, and digital storage media.

In the above-described second embodiment, an example is described in which image registration of CT image data and oral scan image data is performed. However, for various combinations between pieces of 2D image data, between 2D and 3D image data, and between pieces of 3D image data, such as between pieces of CT image data, between pieces of oral scan image data, and between MRI image data and CT image data, etc., the image registration may be performed by detecting the outermost boundary region of the dentition from the outermost boundary region and detecting the central point of the outermost boundary region in the same manner as above. In this case, it is as described above that, when the outermost boundary region of the dentition is detected from the 3D image data, a final outermost boundary region of the dentition may be detected by calculating depth coordinates that are Z-axis coordinates, within a crown length in consideration of the fact that a periphery of the dentition varies depending on the crown length, as well as calculating X-axis and Y-axis coordinates. Further, the above-described second embodiment is also applicable to a multidimensional image including 4D image data in addition to the above-described 3D image data.

Meanwhile, the embodiments of the present invention disclosed in this specification and drawings are only examples to aid understanding of the present invention and the present invention is not limited thereto. It is clear to those skilled in the art that various modifications based on the technological scope of the present invention in addition to the embodiments disclosed herein can be made.

INDUSTRIAL APPLICABILITY

The dental image registration device and method according to the present invention can be used in various dental treatment fields, such as implant surgery and the like.

What is claimed is:

1. A dental image registration device comprising:
    an outermost boundary detection unit configured to detect a first outermost boundary region, which is an outermost boundary region of dentition, from first teeth image data and detect a second outermost boundary region, which is the outermost boundary region of the dentition, from second teeth image data;
    an image registration unit configured to register the first and second teeth image data with respect to a first inscribed circle inscribed in the first outermost boundary region and a second inscribed circle inscribed in the second outermost boundary region or register the first and second teeth image data with respect to a first central point of the first outermost boundary region and a second central point of the second outermost boundary region; and
    an inscribed circle detection unit configured to detect the first inscribed circle inscribed in the first outermost boundary region and detect the second inscribed circle inscribed in the second outermost boundary region,
    wherein the inscribed circle detection unit detects two circles, which have a first radius and are each tangent to both sides that form left and right upper corners of the first and second outermost boundary regions, and one circle, which has the first radius and is tangent to a point at which a bisector line that bisects the first and second outermost boundary regions between the detected two circles abuts with a side that forms a lower end of the first and second outermost boundary regions, as the first and second inscribed circles.

2. The dental image registration device of claim 1, further comprising:
    an inscribed sphere detection unit configured to detect a first inscribed sphere, which is a rotation body of the first inscribed circle, and detect a second inscribed sphere, which is a rotation body of the second inscribed circle,
    wherein the image registration unit registers the first and second teeth image data with respect to the first and second inscribed spheres.

3. The dental image registration device of claim 1, further comprising a central point detection unit configured to detect the first central point of the first outermost boundary region and detect the second central point of the second outermost boundary region,
    wherein the image registration unit registers the first and second teeth image data with respect to the first and second central points.

4. The dental image registration device of claim 2, wherein the image registration unit compares distances between first vertices included in the first inscribed sphere and second vertices included in the second inscribed sphere to register the first and second teeth image data.

5. The dental image registration device of claim 3, wherein the image registration unit compares distances between first vertices included in the first outermost boundary region and second vertices included in the second outermost boundary region to register the first and second teeth image data.

6. The dental image registration device of claim 4, wherein the image registration unit performs the registration of the first and second teeth image data repeatedly until a sum of all the distances between the first and second vertices becomes less than or equal to a reference value.

7. The dental image registration device of claim 4, wherein the image registration unit performs the registration of the first and second teeth image data repeatedly a reference number of times.

8. The dental image registration device of claim 4, further comprising a preprocessor configured to match resolutions of the first and second teeth image data and convert voxel information of the first and second teeth image data into vertex information.

9. The dental image registration device of claim 4, wherein the outermost boundary detection unit detects the first and second outermost boundary regions as polygonal shapes in which each corner is in contact with a most protruding tooth.

10. The dental image registration device of claim 5, wherein the central point detection unit detects the first central point using an average value of X-axis, Y-axis, and Z-axis coordinates of the first vertices and detects the second central point using an average value of X-axis, Y-axis, and Z-axis coordinates of the second vertices.

11. The dental image registration device of claim 4, wherein the outermost boundary detection unit detects the first and second outermost boundary regions from the first and second teeth image data using vertices having a minimum position value and a maximum position value with respect to an X-axis, a Y-axis, and a Z-axis.

12. A dental image registration method comprising:
    detecting a first outermost boundary region, which is an outermost boundary region of dentition, from first teeth image data;
    detecting a second outermost boundary region, which is the outermost boundary region of the dentition, from second teeth image data;
    registering the first and second teeth image data with respect to a first inscribed circle inscribed in the first outermost boundary region and a second inscribed circle inscribed in the second outermost boundary region or registering the first and second teeth image data with respect to a first central point of the first outermost boundary region and a second central point of the second outermost boundary region; and
    detecting each of the first and second inscribed circles inscribed in a corresponding one of the first and second outermost boundary region,
    wherein the step of detecting each of the first and second inscribed circles is a step of detecting two circles, which have a first radius and are each tangent to both sides that form left and right upper corners of the first and second outermost boundary regions, and one circle, which has the first radius and is tangent to a point at which a bisector line that bisects the first and second outermost boundary regions between the detected two circles abuts with a side that forms a lower end of the first and second outermost boundary regions, as the first and second inscribed circles.

13. The dental image registration method of claim 12, wherein the registering of the first and second teeth image data includes:
    detecting each of the first and second inscribed spheres, which is a rotation body of a corresponding one of the first and second inscribed circle; and
    registering the first and second teeth image data with respect to the first and second inscribed sphere.

14. The dental image registration method of claim 12, wherein the registering of the first and second teeth image data includes:
  detecting the first and second central points of the first and second outermost boundary regions; and
  registering the first and second teeth image data with respect to the first and second central points.

15. The dental image registration device of claim 5, wherein the image registration unit performs the registration of the first and second teeth image data repeatedly until a sum of all the distances between the first and second vertices becomes less than or equal to a reference value.

16. The dental image registration device of claim 5, wherein the image registration unit performs the registration of the first and second teeth image data repeatedly a reference number of times.

17. The dental image registration device of claim 5, further comprising a preprocessor configured to match resolutions of the first and second teeth image data and convert voxel information of the first and second teeth image data into vertex information.

18. The dental image registration device of claim 5, wherein the outermost boundary detection unit detects the first and second outermost boundary regions as polygonal shapes in which each corner is in contact with a most protruding tooth.

19. The dental image registration device of claim 5, wherein the outermost boundary detection unit detects the first and second outermost boundary regions from the first and second teeth image data using vertices having a minimum position value and a maximum position value with respect to an X-axis, a Y-axis, and a Z-axis.

* * * * *